United States Patent [19]

Domet et al.

[11] Patent Number: 4,929,605

[45] Date of Patent: May 29, 1990

[54] PHARMACEUTICAL COMPOSITION FOR PIPERIDINOALKANOL DERIVATIVES

[75] Inventors: Jack Domet; Dhiren N. Shah, both of Cincinnati, Ohio

[73] Assignee: Merrell Dow Pharmaceuticals Inc., Cincinnati, Ohio

[21] Appl. No.: 325,254

[22] Filed: Mar. 17, 1989

Related U.S. Application Data

[63] Continuation-in-part of Ser. No. 152,689, Feb. 5, 1988, abandoned, which is a continuation-in-part of Ser. No. 117,166, Nov. 4, 1987, abandoned, which is a continuation-in-part of Ser. No. 105,928, Oct. 7, 1987, abandoned.

[51] Int. Cl.$^5$ ............... A61K 31/44; A61K 9/20; A61K 47/00
[52] U.S. Cl. ................. 514/54; 424/465; 424/466; 514/317; 514/326; 514/826; 514/960
[58] Field of Search ............... 514/317, 326, 826, 960, 514/54; 424/156, 465, 466

[56] References Cited

U.S. PATENT DOCUMENTS

| | | | |
|---|---|---|---|
| 3,878,217 | 4/1975 | Carr et al. | 514/826 |
| 4,254,129 | 3/1981 | Carr et al. | 514/317 |
| 4,285,957 | 8/1981 | Carr et al. | 514/317 |
| 4,533,543 | 8/1985 | Morris et al. | 424/441 |

FOREIGN PATENT DOCUMENTS 0264259 4/1988 European Pat. Off. .

OTHER PUBLICATIONS

Chemical Abstracts, vol. 86, No. 26, Jun. 27, 1977, abstract 86:195167R.

*Primary Examiner*—Ronald W. Griffin
*Attorney, Agent, or Firm*—Louis J. Wille

[57] ABSTRACT

A pharamaceutical composition in solid unit dosage form comprising (a) a therapeutically effective amount of a piperidinoalkanol compound, or a pharmaceutically acceptable salt thereof, (b) pharmaceutically acceptable nonionic or cationic surfactant in an amount of from about 0.1% to about 6% by weight of the composition, and (c) pharmaceutically acceptable carbonate salt in an amount of from about 2% to about 50% by weight of the composition.

20 Claims, No Drawings

PHARMACEUTICAL COMPOSITION FOR PIPERIDINOALKANOL DERIVATIVES

This is a continuation-in-part of application Ser. No. 152,689, filed Feb. 5, 1988, now abandoned, which is a continuation-in-part of application Ser. No. 117,166, filed Nov. 4, 1987, now abandoned, which is a continuation-in-part of application Ser. No. 105,928, filed Oct. 7, 1987, now abandoned.

BACKGROUND OF THE INVENTION

Various piperidinoalkanol derivatives are disclosed in U.S. Pat. Nos. 3,878,217, 4,254,129, and 4,285,957 as compounds useful as antihistamines, antiallergy agents, and bronchodilators. Included within the scope of these generically defined piperidinoalkanols is α-[4-(1,1-dimethylethyl)phenyl]-4-(hydroxydiphenylmethyl)-1-piperidinebutanol which is commercially available as a pharmaceutical composition in solid unit dosage form for the treatment of patients with symptoms of seasonal allergic rhinitis.

In general, these piperidinoalkanol derivatives are only minimally soluble in water and therefore the therapeutically inactive ingredients in a pharmaceutical composition containing one or more of these compounds are very important in providing for their efficient and immediate absorption and bioavailability after oral administration.

A novel pharmaceutical composition is now provided which allows efficient and immediate absorption and bioavailability of these compounds after oral administration thereof.

DETAILED DESCRIPTION OF THE INVENTION

The present invention relates to a pharmaceutical composition for oral administration of various piperidinoalkanol derivatives which are disclosed in U.S. Pat. Nos. 3,878,217, 4,254,129, and 4,285,957, the full disclosures of each patent being incorporated herein by reference. These compounds are useful as antihistamines, antiallergy agents, and bronchodilators and are described by the formulas (1), (2), and (3).

Compounds of formula (1) are those which correspond to the formula

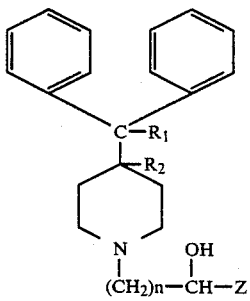

(1)

wherein $R_1$ is hydrogen or hydroxy; $R_2$ is hydrogen; or $R_1$ and $R_2$ taken together form a second bond between the carbon atoms bearing $R_1$ and $R_2$; n is a positive whole integer of from 1 to 3; Z is thienyl, phenyl or substituted phenyl wherein the substituents on the substituted phenyl may be attached at the ortho, meta, or para positions of the substituted phenyl ring and are selected from the group consisting of a halogen atom, a straight or branched lower alkyl chain of from 1 to 4 carbon atoms, a lower alkoxy group of from 1 to 4 carbon atoms, a di(lower)alkylamino group, or a saturated monocyclic heterocyclic ring selected from the group consisting of pyrolidino, piperidino, morpholino, or N-(lower)alkylpiperizino, or pharmaceutically acceptable acid addition salts thereof Compounds of formula (2) are those which correspond to the formula

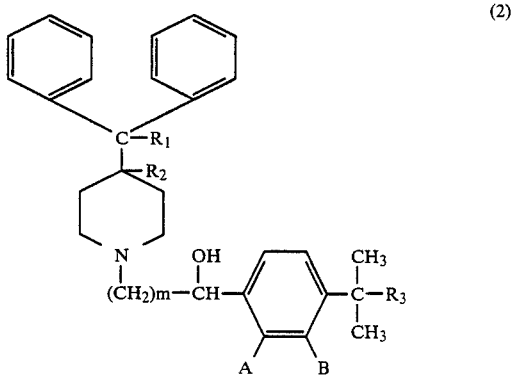

(2)

wherein $R_1$ represents hydrogen or hydroxy; $R_2$ represents hydrogen; or $R_1$ and $R_2$ taken together form a second bond between the carbon atoms bearing $R_1$ and $R_2$; m is an integer of from 1 to 5; $R_3$ is —$CH_3$, or —$CH_2OH$; each of A and B is hydrogen or hydroxy; with the provisos that at least one of A or B is hydrogen and one of A or B is other than hydrogen when $R_3$ is —$CH_3$; and pharmaceutically acceptable salts and individual optical isomers thereof.

Compounds of formula (3) are those which correspond to the formula

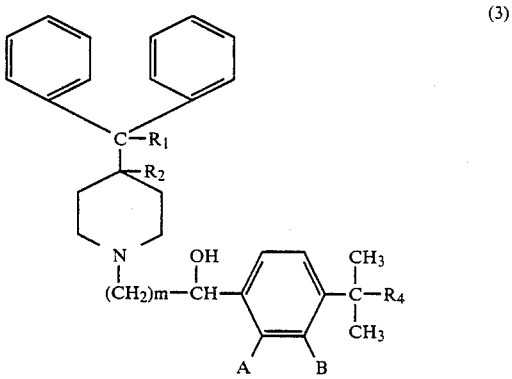

(3)

wherein $R_1$ represents hydrogen or hydroxy; $R_2$ represents hydrogen; or $R_1$ and $R_2$ taken together form a second bond between the carbon atoms bearing $R_1$ and $R_2$; m is an integer of from 1 to 5; $R_4$ is —COOH or —COOalkyl wherein the alkyl moiety has from 1 to 6 carbon atoms and is straight or branched; each of A and B is hydrogen or hydroxy; with the proviso that at least one of A or B is hydrogen; and pharmaceutically acceptable salts and individual optical isomers thereof.

The pharmaceutical compositions for oral administration provided by the present invention comprise a therapeutically effective amount of a piperidinoalkanol compound of formula (1), (2), or (3) associated with pharmaceutically acceptable carbonate salt in an amount ranging from about 2% to about 50% by weight of the composition, and pharmaceutically acceptable nonionic or a cationic surfactant in an amount ranging from about 0.1% to about 6% by weight of the composition In addition, the pharmaceutical compositions of the present invention can optionally contain one or more other therapeutically inert ingredients as are well known and appreciated in the art of pharmaceutical science.

The pharmaceutical composition of the present invention is administered orally in the form of a solid unit dosage form such as tablets, coated tablets, powders, dragees, hard or soft gelatin capsules. The preferred solid unit dosage forms of the present invention are tablets, coated tablets and capsules. A unit dose is that amount of the pharmaceutical composition which is individually administered.

A therapeutically effective amount of a piperidinoalkanol compound of formula (1), (2), or (3) is that amount which produces the desired therapeutic response (i.e., antihistaminic, antiallergic, or bronchodilatory effect) upon oral administration according to a single or multiple dosage regimen. An effective amount may vary over a wide range from about 0.01 to about 20 milligrams (mg) per kilogram (kg) of body weight per dose. A pharmaceutical composition which provides from about 10 mg to about 150 mg per unit dose is preferred. Pharmaceutical compositions which provide from about 40 mg to about 70 mg per unit dose and those which provide from about 110 mg to about 130 mg are especially preferred. The compound $\alpha$-[4-(1,1-dimethylethyl)phenyl]-4-(hydroxydiphenylmethyl)-1-piperidinebutanol is the preferred therapeutically active ingredient.

According to the present invention, the term "pharmaceutically acceptable nonionic surfactant" means and includes various pharmaceutically acceptable long chain fatty acid esters of polyoxyethylene sorbitan, such as polysorbate 80 (also known as Tween 80), and various poloxamers or pluronics, such as Pluronic-F68, or mixtures thereof. These nonionic surfactants are well known and appreciated in the art of pharmaceutical science. The preferred nonionic surfactants in the pharmaceutical composition of the present invention are the polyoxyethylene sorbitan fatty acid esters with polysorbate 80 being especially preferred.

According to the present invention, the term "pharmaceutically acceptable cationic surfactant" means and includes various pharmaceutically acceptable ionic compounds with a positively charged ionic species containing relatively hydrophobic regions. Typically these surfactants are quaternary ammonium salts, such as for example, cetylpyridium chloride, cetyl trimethyl ammonium bromide and benzalkonium chloride. The preferred cationic surfactant for purposes of the present invention is cetylpyridium chloride The amount of the nonionic or cationic surfactant in the pharmaceutical composition of the present invention can vary from about 0.1% to about 6% by weight. The preferred amount is from about 2% to about 4% by weight with about 3% being most preferred.

According to the present invention, the term "pharmaceutically acceptable carbonate salt" means and includes pharmaceutically acceptable inorganic carbonate and bicarbonate salts, as are well known and appreciated in the art, such as calcium carbonate and sodium bicarbonate, or mixtures thereof. Calcium carbonate is the preferred carbonate salt according to the present invention.

The amount of carbonate salt present in the pharmaceutical composition of the present invention can vary from about 2% to about 50% by weight. The preferred amount of carbonate salt is from about 2% to about 25% by weight with from about 12% to about 18% being most preferred and about 15% being especially preferred.

The pharmaceutical composition of the present invention can optionally contain one or more other therapeutically inert ingredients such as are well known and appreciated in the art of pharmaceutical science. Such therapeutically inert ingredients include: binders such as pregelatinized starch, povidone, cellulose derivatives including methylcellulose, hydroxypropyl methylcellulose, and the like; conventional carriers and fillers such as lactose, corn starch, microcrystalline cellulose, and the like; lubricants such as magnesium stearate, calcium stearate, zinc stearate, stearic acid, talc, hydrogenated vegetable oil and the like; glidants such as silicon dioxide and the like; disintegrents such as corn starch derivatives (e.g., starch glycolate sodium) and the like; sweetening agents; coloring agents; flavoring agents; antioxidants; and the like. These additional ingredients can be present in amounts up to about 95% of the total composition weight. Selection of a particular ingredient or ingredients and the amounts used can be readily determined by one skilled in the art by reference to standard procedures and practices with respect to the particular dosage form selected. A preferred combination of additional ingredients for a solid unit dosage form include microcrystalline cellulose, pregelatinized corn starch, starch glycolate sodium, and magnesium stearate in preferred amounts of about 25 to 45%, 20 to 40%, 1 to 10%, and 0.1 to 1.0%, respectively, with about 35%, 30%, 5%, and 0.5% of each, respectively, being most preferred. The above amounts represent percent by weight of the composition.

The ingredients of the pharmaceutical composition according to the present invention are brought together into a dosage form for oral administration according to standard practices and procedures well known in the art of pharmaceutical science using conventional formulation and manufacturing techniques.

In a preferred embodiment of the present invention, solid dosage units are formulated and manufactured in tablet form using the following procedure:

An aqueous solution of the nonionic or cationic surfactant and other water-soluble ingredients (if any) is intermixed with a piperidinoalkanol compound (such as $\alpha$-[4-(1,1-dimethylethyl]phenyl]-4-(hydroxydiphenylmethyl)-1-piperidinebutanol), any microcrystalline cellulose, any calcium carbonate (total amount or a portion), and any pregelatinized corn starch. The granules thus formed are dried and milled to uniform size and then intermixed with any remaining ingredients, such as any remaining portion of calcium carbonate, silicon dioxide amorphous, pregelatinized corn starch, starch glycolate sodium, magnesium stearate, or any sodium bicarbonate. The complete mixture is then subjected to tableting in conventional tableting machines under conventional conditions.

It is of course understood that tablets produced according to the present invention can be film or sugar coated using standard ingredients and procedures commonly used and well known in the art of pharmaceutical science. It is contemplated that tablets so coated are within the scope of the present invention.

The pharmaceutical composition of the present invention demonstrates acceptable in vitro dissolution characteristics and provides efficient bioavailability of the therapeutically active ingredient in an immediate release manner The following examples are illustrative of preferred embodiments of the present invention and are not intended to limit the scope of the present invention in any way:

EXAMPLE 1

60 Mg Tablets for Oral Administration

Combine 360 grams (g) of α-[4-(1,1-dimethylethyl)-phenyl]-4-(hydroxydiphenylmethyl)-1-piperidinebutanol, 1150 g of microcrystalline cellulose, 495 g of calcium carbonate (heavy), and 743 g of pregelatinized corn starch and blend in a mixer for 10 minutes (min). To this mixture add a solution of 99 g of polysorbate 80 in 1.9 liters (L) of purified water and continue mixing until a good granulation is formed.

Pass the granulation through a 10-mesh screen and dry at 120 degrees Fahrenheit (°F.) for about 17 hours to a moisture content of about 2.0% to about 2.5% as measured by an O'Haus moisture meter under metering conditions of 40 volts for 20 min. Pass the dried granulation through a 14-mesh screen.

To the granulation add 264 g of pregelatinized corn starch, 165 g of starch glycolate sodium, and 18.15 g of magnesium stearate and mix for about 2 min.

Compress tablets at a weight of 550 milligrams (mg) and a hardness of about 9 to 10 kilopounds (kp) using a tablet press equipped with 13/32 inch, round, flat-face, beveled edge tooling.

This procedure results in about 6000 tablets of the following composition:

| INGREDIENT | AMOUNT mg/tablet | COMPOSITION % by weight |
|---|---|---|
| Therapeutically Active Ingredient* | 60.0 | 10.9 |
| Polysorbate 80 | 16.5 | 3.0 |
| Calcium Carbonate | 82.5 | 15.0 |
| Microcrystalline cellulose | 192.5 | 35.0 |
| Pregelatinized Corn Starch | 167.8 | 30.5 |
| Starch Glycolate Sodium | 27.5 | 5.0 |
| Magnesium Stearate | 3.025 | 0.55 |

*α-[4-(1,1-dimethylethyl)phenyl]-4-(hydroxydiphenylmethyl)-1-piperidinebutanol

Use the U.S.P. Paddle Method to determine the dissolution characteristics of the tablets made by the above method. Place a tablet in a U.S.P. Rotating Paddle Apparatus set at 50 revolutions-per-minute (rpm) in 900 milliliters (ml) of deaerated 0.1 N hydrochloric acid maintained at 37∓5 degrees Celsius (°C.). After 60 min withdraw an aliquot of the dissolution medium and assay for α-[4-(1,1dimethylethyl)phenyl]-4-(hydroxydiphenylmethyl)-1-piperidinebutanol by High Performance Liquid Chromatography (HPLC).

The results of the dissolution averaged for 6 tablets indicate that, after 60 min, 87.8% of the α-[4-(1,1-dimethylethyl)phenyl]-4-(hydroxydiphenylmethyl)-1-piperidinebutanol is released into the dissolution medium (range 86.1% to 89.2%).

Tablets with the same composition as above except that cetylpyridium chloride is used instead of polysorbate 80 are prepared in a manner analogous to that described above. The results of the dissolution averaged for 3 such tablets indicate that, after 60 min, 103% of the α-[4-(1,1-dimethylethyl)phenyl]-4-(hydroxydiphenylmethyl)-1-piperidinebutanol is released into the dissolution medium (range 102% to 105%).

EXAMPLE 2

120 Mg Tablets for Oral Administration

Combine 360 g of α-[4-(1,1-dimethylethyl)phenyl]-4-(hydroxydiphenylmethyl)-1-piperidinebutanol, 724 g of microcrystalline cellulose, 338 g of calcium carbonate (heavy), and 502.5 g of pregelatinized corn starch and blend in a mixer for 10 min. To this mixture add a solution of 67.5 g of polysorbate 80 in 1250 ml of purified water and continue mixing until a good granulation is formed.

Pass the granulation through a 10-mesh screen and dry at 140° F. for about 15 hours to a moisture content of about 2.0% to about 2.5% as measured by a Computrac Moisture Analyzer at 100° C. Pass the dried granulation through a 16-mesh screen.

To the granulation add 178.5 g of pregelatinized corn starch, 67.5 g of starch glycolate sodium and mix for about 3 min. To this mixture, add 12.6 g of magnesium stearate and mix for about 2 min.

Compress tablets at a weight of 750 mg and a hardness of about 9 to 10 kp using a tablet press equipped with 15/32 inch, round, flat-face, beveled edge tooling.

This procedure results in about 3000 tablets of the following composition:

| INGREDIENT | AMOUNT mg/tablet | COMPOSITION % by weight |
|---|---|---|
| Therapeutically Active Ingredient* | 120 | 16.0 |
| Polysorbate 80 | 22.5 | 3.0 |
| Calcium Carbonate | 112.5 | 15.0 |
| Microcrystalline cellulose | 241.3 | 32.2 |
| Pregelatinized Corn Starch | 227.0 | 30.3 |
| Starch Glycolate Sodium | 22.5 | 3.0 |
| Magnesium Stearate | 4.2 | 0.56 |

*α[4-(1,1-dimethylethyl)phenyl]-4-(hydroxydiphenylmethyl)-1-piperidinebutanol

Use the U.S.P. Paddle Method to determine the dissolution characteristics of the tablets made by the above method. Place a tablet in a U.S.P. Rotating Paddle Apparatus set at 50 rpm in 900 ml of de-aerated 0.1 N hydrochloric acid maintained at 37∓5° C. After 45 min withdraw an aliquot of the dissolution medium and assay for α-[4-(1,1-dimethylethyl)phenyl]-4-(hydroxydiphenylmethyl)-1-piperidinebutanol by HPLC.

The results of the dissolution averaged for 6 tablets indicate that, after 45 min, 85.9% of the α-[4-(1,1-dimethylethyl)phenyl]-4-(hydroxydiphenylmethyl)-1-piperidinebutanol is released into the dissolution medium (range 82% to 89%).

We claim:
1. A pharmaceutical composition in solid unit dosage form comprising (a) a therapeutically effective amount of a piperidinoalkanol compound, or a pharmaceutically acceptable salt thereof, (b) pharmaceutically acceptable nonionic surfactant in an amount of from about

0.1% to about 6% by weight of the composition, and (c) pharmaceutically acceptable carbonate salt in an amount of from about 2% to about 50% by weight of the composition.

2. A pharmaceutical composition according to claim 1 wherein the carbonate salt is calcium carbonate.

3. A pharmaceutical composition according to claim 2 wherein the piperidinoalkanol is α-[4-(1,1-dimethylethyl)phenyl]-4-(hydroxydiphenylmethyl)-1-piperidinebutanol.

4. A composition according to claim 3 wherein the α-[4-(1,1-dimethylethyl)phenyl]-4-(hydroxydiphenylmethyl)-1-piperidinebutanol is present in the amount of about 60 mg.

5. A composition according to claim 3 wherein the α-[4-(1,1-dimethylethyl)phenyl]-4-(hydroxydiphenylmethyl)-1-piperidinebutanol is present in the amount of about 120 mg.

6. A composition according to claim 4 or 5 wherein the nonionic surfactant is present in an amount of from about 2% to about 4% by weight of the composition.

7. A composition according to claim 4 or 5 wherein the nonionic surfactant is present in an amount of about 3% by weight of the composition.

8. A composition according to claim 4 wherein the nonionic surfactant is polysorbate 80.

9. A composition according to claim 5 wherein the nonionic surfactant is polysorbate 80.

10. A composition according to claim 4 or 5 wherein calcium carbonate is present in an amount of from about 2% to about 25% by weight of the composition.

11. A composition according to claim 4 or 5 wherein the calcium carbonate is present in an amount of from about 12% to about 18% by weight of the composition.

12. A composition according to claim 4 or 5 wherein the calcium carbonate is present in an amount of about 15% by weight of the composition.

13. A composition according to claim 8 wherein polysorbate 80 and calcium carbonate are present in amounts of about 3% and 15%, respectively, by weight of the composition, and further comprises, microcrystalline cellulose, pregelatinized corn starch, sodium starch glycolate and magnesium stearate in amounts of about 35%, 30%, 5%, and 0.5%, respectively, by weight of the composition.

14. A composition according to claim 9 wherein polysorbate 80 and calcium carbonate are present in amounts of about 3% and 15%, respectively, by weight of the composition, and further comprises, microcrystalline cellulose, pregelatinized corn starch, sodium starch glycolate and magnesium stearate in amounts of about 32%, 30%, 3%, and 0.5%, respectively, by weight of the composition.

15. A pharmaceutical composition in solid unit dosage form comprising (a) a therapeutically effective amount of a piperidinoalkanol compound, or a pharmaceutically acceptable salt thereof, (b) pharmaceutically acceptable cationic surfactant in an amount of from about 0.1% to about 6% by weight of the composition, and (c) pharmaceutically acceptable carbonate salt in an amount of from about 2% to about 50% by weight of the composition.

16. A composition according to claim 15 wherein the carbonate salt is calcium carbonate.

17. A composition according to claim 16 wherein the piperidinoalkanol compound is piperidinoalkanol is α-[4-(1,1-dimethylethyl)phenyl]-4-(hydroxydiphenylmethyl)-1-piperidinebutanol.

18. A composition according to claim 17 wherein the piperidinoalkanol is present in an amount of from about 10 mg to about 120 mg.

19. A composition according to claim 18 wherein the cationic surfactant is cetylpyridium chloride.

20. A composition according to claim 19 wherein cetylpyridium chloride and calcium carbonate are present in amounts of about 3% and 15%, respectively, by weight of the composition, and further comprises, microcrystalline cellulose, pregelatinized corn starch, sodium starch glycolate and magnesium stearate in amounts of about 35%, 30%, 5%, and 0.5%, respectively, by weight of the composition.

* * * * *